US009014454B2

(12) United States Patent
Zankowski

(10) Patent No.: US 9,014,454 B2
(45) Date of Patent: Apr. 21, 2015

(54) METHOD AND APPARATUS PERTAINING TO IMAGES USED FOR RADIATION-TREATMENT PLANNING

(75) Inventor: Corey E. Zankowski, San Jose, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 614 days.

(21) Appl. No.: 13/112,030

(22) Filed: May 20, 2011

(65) Prior Publication Data

US 2012/0294497 A1  Nov. 22, 2012

(51) Int. Cl.
*G06K 9/00* (2006.01)
*A61N 5/10* (2006.01)
*G06T 7/00* (2006.01)

(52) U.S. Cl.
CPC .......... *A61N 5/1038* (2013.01); *G06T 7/0012* (2013.01); *G06T 7/0028* (2013.01); *G06T 2207/20016* (2013.01); *G06T 2207/30004* (2013.01)

(58) Field of Classification Search
USPC ......... 382/128, 131, 132; 348/135; 378/4, 20, 378/21, 163, 165; 702/40; 250/341.1, 250/363.04, 370.08
See application file for complete search history.

(56) References Cited

U.S. PATENT DOCUMENTS

| | | | |
|---|---|---|---|
| 5,901,199 A * | 5/1999 | Murphy et al. | 378/65 |
| 6,516,046 B1 * | 2/2003 | Frohlich et al. | 378/65 |
| 6,728,424 B1 * | 4/2004 | Zhu et al. | 382/294 |
| 6,950,542 B2 * | 9/2005 | Roesch et al. | 382/128 |
| 7,046,831 B2 * | 5/2006 | Ruchala et al. | 382/131 |
| 7,171,255 B2 * | 1/2007 | Holupka et al. | 600/427 |
| 7,231,076 B2 | 6/2007 | Fu et al. | |
| 7,935,939 B2 * | 5/2011 | Aoi et al. | 250/491.1 |
| 8,190,233 B2 * | 5/2012 | Dempsey | 600/411 |
| 2002/0077543 A1 * | 6/2002 | Grzeszczuk et al. | 600/424 |
| 2002/0188194 A1 * | 12/2002 | Cosman | 600/426 |
| 2003/0225325 A1 * | 12/2003 | Kagermeier et al. | 600/407 |
| 2004/0092815 A1 * | 5/2004 | Schweikard et al. | 600/425 |
| 2004/0252873 A1 * | 12/2004 | Avinash et al. | 382/132 |
| 2005/0053267 A1 * | 3/2005 | Mostafavi | 382/128 |
| 2005/0059887 A1 * | 3/2005 | Mostafavi et al. | 600/427 |
| 2005/0084178 A1 * | 4/2005 | Lure et al. | 382/294 |

(Continued)

OTHER PUBLICATIONS

Fornefett et al., "Elastic Medical Image Registration Using Orientation Attributes at Landmarks," in E. Berry, D. Hogg, K.V. Mardia, M.A. Smith (Eds.), University of Leeds 1998, 4 pages.

(Continued)

*Primary Examiner* — Shervin Nakhjavan
(74) *Attorney, Agent, or Firm* — Fitch, Even, Tabin & Flannery LLP

(57) ABSTRACT

A radiation-treatment planning apparatus accesses first information regarding a first image that pertains to a patient's body at a first time as well as second information regarding a second image that pertains to the patient's body at a second, later time. The radiation-treatment planning apparatus then correlates components of the patient's body as appear in the second image with components that appear in the first image while treating the components as comprising rigid structures regardless of whether those components, in fact, are rigid structures. The first information can include segmentation information as pertains to the components. These teachings will accommodate a wide range of components including, but not limited to, organs, portions of organs, and even implanted man-made objects.

7 Claims, 5 Drawing Sheets

(56) References Cited

U.S. PATENT DOCUMENTS

| | | |
|---|---|---|
| 2005/0201516 A1* | 9/2005 | Ruchala et al. ............... 378/65 |
| 2007/0116381 A1 | 5/2007 | Khamene |
| 2007/0179377 A1 | 8/2007 | Carlsen et al. |
| 2008/0039713 A1* | 2/2008 | Thomson et al. ............ 600/411 |
| 2008/0109013 A1* | 5/2008 | Fu et al. ..................... 606/130 |
| 2008/0130825 A1* | 6/2008 | Fu et al. ........................... 378/8 |
| 2008/0159612 A1* | 7/2008 | Fu et al. ..................... 382/131 |
| 2009/0187422 A1* | 7/2009 | Kaus et al. ..................... 705/2 |
| 2009/0225932 A1* | 9/2009 | Zhu et al. ......................... 378/7 |
| 2010/0145193 A1* | 6/2010 | Florent et al. ................ 600/427 |
| 2010/0266188 A1* | 10/2010 | Burns et al. ................. 382/132 |
| 2010/0329414 A1* | 12/2010 | Zhu et al. ......................... 378/4 |

OTHER PUBLICATIONS

Matuszewski et al., "Elastic Image Matching with Embedded Rigid Structures Using Spring-Mass System," IEEE International Conference on Image Processing, ICIP 2003, 4 pages.

Malsch et al., "An Enhanced Block Matching Algorithm for Fast Elastic Registration in Adaptive Radiotherapy," Phys. Med. Biol. 51 (2006), pp. 4789-4806.

* cited by examiner

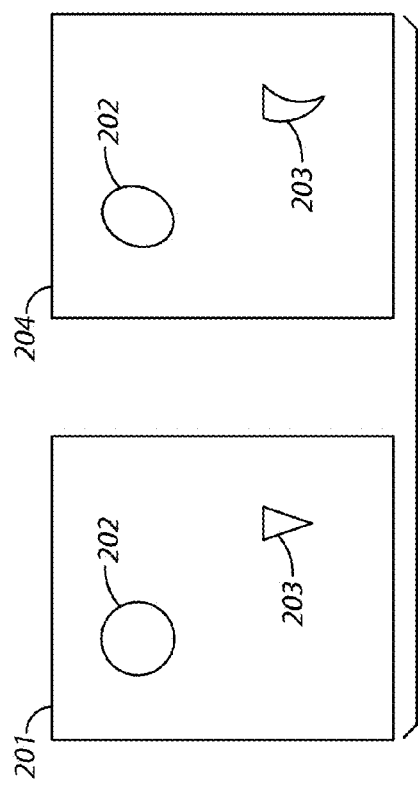
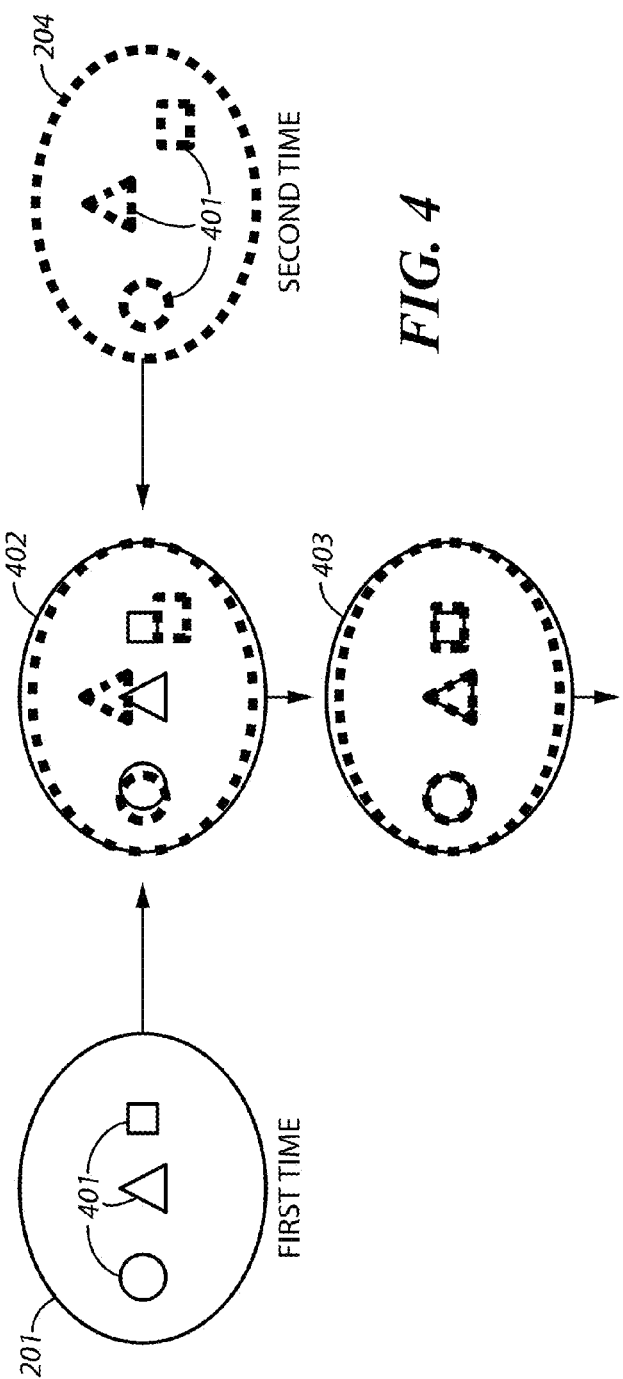
FIG. 3
FIG. 4

METHOD AND APPARATUS PERTAINING TO IMAGES USED FOR RADIATION-TREATMENT PLANNING

TECHNICAL FIELD

This invention relates generally to radiation-treatment planning and more particularly to images used for such purposes.

BACKGROUND

Radiation therapy is known in the art. Generally speaking, such therapy involves exposing an unwanted volume on or within a patient's body to high-energy radiation (such as, but not limited to, x-rays). This radiation often serves to destroy the irradiated cellular material and hence reduce or eliminate the unwanted volume. In many cases such radiation is periodically administered over time (days, weeks, or months).

Unfortunately, this radiation does not inherently discriminate between wanted and unwanted portions of the patient's body. Treatment plans are therefore formulated to both ensure appropriate irradiation of the unwanted volume while at least attempting, in various ways, to minimize exposing wanted volumes to the radiation. These treatment plans are often based, at least in part, upon images (such as x-ray images) that include the patient's treatment volume.

In many cases the patient's physical circumstances will change over the course of such a treatment regimen or even subsequent to planning the treatment but prior to administering that treatment. The unwanted volume itself, for example, can become reduced in size, change its orientation or shape, and/or move in some respect. As another example, the patient themselves may gain, or lose, weight. And as yet another example, other structures within the patient can change shape, location, or orientation. To accommodate such changes, it is known to update the information available to the treatment-planning process during the overall course of a protracted treatment regimen.

Updating the treatment plan can comprise obtaining a new image of the patient's relevant anatomy prior to a given treatment session. One can then employ deformable registration techniques to modify a treatment plan that presumes a first (earlier) anatomical configuration to now correlate to a present anatomical configuration for the patient. Unfortunately, typical deformable registration practices are computationally intensive (in order to accurately accommodate the numerous ways in which a patient's anatomy can vary from a prior presentation) and this can lead to expensive equipment requirements, treatment delay, or both.

BRIEF DESCRIPTION OF THE DRAWINGS

The above needs are at least partially met through provision of the method and apparatus pertaining to images used for radiation-treatment planning described in the following detailed description, particularly when studied in conjunction with the drawings, wherein:

FIG. 3 comprises a top plan schematic representation as configured in accordance with various embodiments of the invention;

FIG. 4 comprises a top plan schematic representation as configured in accordance with various embodiments of the invention;

Figure 1:
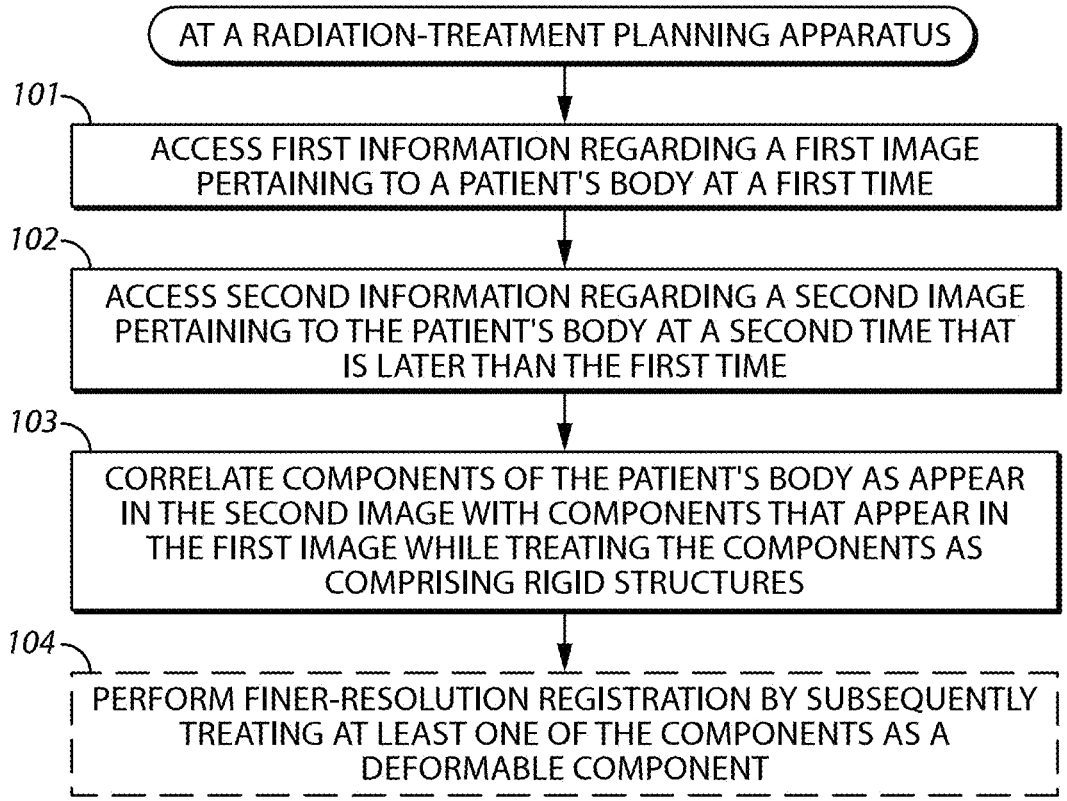
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments can be carried out by an appropriately-configured radiation-treatment planning apparatus. These teachings will also accommodate, however, using a dedicated-purpose apparatus that serves only to carry out the described steps and to make the described correlated results available to such a radiation-treatment planning apparatus. (Accordingly, for the sake of convenience, as used herein the expression "radiation-treatment planning apparatus" will be understood to include both such examples.)

Pursuant to these teachings a radiation-treatment planning apparatus accesses first information regarding a first image that pertains to a patient's body at a first time as well as second information regarding a second image that pertains to the patient's body at a second, later time. The radiation-treatment planning apparatus then correlates components of the patient's body as appear in the second image with components that appear in the first image while treating the components as comprising rigid structures regardless of whether those components, in fact, are rigid structures.

By one approach, the aforementioned first information can include segmentation information as pertains to the components. These teachings will accommodate a wide range of components including, but not limited to, organs, portions of organs, and even implanted man-made objects.

By one approach the radiation-treatment planning apparatus can conduct the aforementioned correlation in parallel for some or even all of the components of the first image.

This correlation activity can comprise, for example, identifying components in the second image to provide identified components and then determining relative positions amongst the identified components to thereby perform a course registration with respect to the first image. If desired, these teachings will then optionally accommodate performing a finer-resolution registration by subsequently treating at least one of the components as a deformable component.

So configured, a radiation-treatment planning apparatus can arrive at suitable results in a less computationally-intensive manner. This, in turn, reduces system requirements and/or reduces the delay experienced by a patient and the treatment facility between when the technician captures that second image and when the treatment begins.

These teachings are readily employed in conjunction with existing radiographic studies and treatment-planning methodologies and hence can serve to greatly leverage the presence of such information, processes, and equipment. These teachings are also highly scalable and can be employed across a wide variety of methodologies and equipment.

These and other benefits may become clearer upon making a thorough review and study of the following detailed description. Referring now to the drawings, and in particular to FIG. 1, an illustrative process 100 that is compatible with many of these teachings will now be presented. As noted earlier this process 100 can be carried out by any of a variety of radiation-treatment planning apparatuses.

At step 101 of this process 100 the radiation-treatment planning apparatus accesses first information regarding a first image that pertains to a patient's body at a first time. This "time" might be, for example, when diagnostic images or initial treatment-planning images were first captured for this patient. In any event this first time will typically be some time in the past, often many weeks or even months (with even longer periods being possible and permissible).

The first image may comprise a complete view of the patient but in many application settings will only include some components of interest (such as one or more organs, organ portions, implanted man-made objects, and so forth). The first image itself can comprise, for example, a two-dimensional or three-dimensional x-ray-based image of the patient but other image-capturing methodologies and technologies are known in the art and these teachings are not especially sensitive to any particular choice in these regards so long as the anatomical feature(s) of interest is directly or indirectly discernable to some useful degree.

By one non-limiting approach, the aforementioned first information regarding this first image can comprise segmentation information as pertains to the components in that image. Segmentation is known in the art and refers to the practice of identifying components in an image with corresponding textual names, categorizations, or the like. Segmentation information for a two-dimensional x-ray image of a patient's chest, for example, might include the word "lung" as associated with the patient's lungs and "heart" as associated with the patient's heart. The degree of hierarchical segmentation (for example, the level of parsing that one applies to a given component) can of course vary with the needs of the application setting.

At step 102 this process accesses second information regarding a second image pertaining to the patient's body at a second time that is later than the first time. In many application settings this second time will be just prior (by, for example, a few minutes) to the administration of a radiation-treatment dosing as per a given previously-approved radiation-treatment plan. Accordingly, in many application settings this second time will often post date the aforementioned first time by many weeks or even months (with even longer periods being possible).

This second image can represent a same image-capture modality as the first image if desired. For example, both the first and the second image can be two-dimensional x-ray images. This, however, is not a requirement. In fact, in some application settings or for some purposes it may be useful for the second image to be captured by a different image-capture modality than the first image.

Generally speaking, the first and second images should coincide at least to some degree in that both images, for many application purposes, should include the component or components of particular interest to the treatment process (for example, as a treatment target, a component to be avoided during treatment, or a component that simply serves as a useful registration point or landmark). These teachings do not require, however, that the first and second images share an identical field of view nor even, necessarily, an identical perspective or proximity.

Generally speaking, this accessing of the first information and the second information comprises accessing one or more digital memories and accessing this information in digital form.

Also generally speaking, it will not be unexpected that the same components as appear in both the first and second images will differ in their respective views. These differences can occur even when a same image-capture modality applies for both images and when the field of view and other image-capture characterizing parameters are otherwise identical for both images.

Figure 2:
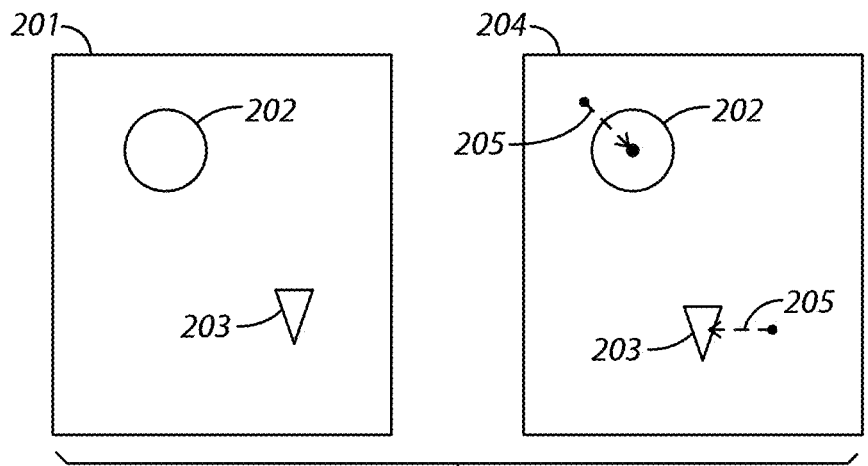
FIG. 2 comprises a top plan schematic representation as configured in accordance with various embodiments of the invention.

Referring momentarily to FIG. 2, such differences can happen, for example, because one or more of the components of interest experience relative movement between the first time (which refers to the capture of the first image) and the second time (which refers to the capture of the second image). In this illustrative example, the first image 201 includes a first component 202 (such as an organ) and a second component 203 (such as an implanted man-made object). In the later-captured second image 204, both of these components 202 and 203 have moved from their earlier positions as denoted by the arrows 205. As illustrated, it is of course possible for each component to move in an individually different manner.

Referring now momentarily to FIG. 3, such differences can also happen, for example, because one or more of the components of interest themselves undergo some change in shape and/or size. As a simple illustrative example in these regards, the circular-shaped component 202 in the first image 201 appears more oval-like in the second image 204. The triangle-shaped component 203 in the first image 201, for its part, has curved rather than straight edges in the second image 204 (such a change might be cause by a literal change in the shape of the component or may simply occur because the component has, for example, rotated to thereby present a different profile).

The fact that components within a patient's body can change relative position amongst themselves and can also change shape and/or size complicates the current identification of components in a patient immediately prior to administering a radiation-treatment dosage. At step 103 of this process 100 the radiation-treatment planning apparatus correlates one or more components of the patient's body as appear in the second image with components that appear in the first image while treating the components as comprising rigid structures.

In many cases, of course, one or more of these components are not rigid structures. As illustrated above, some components (such as any of a variety of organs or parts of organs) are distinctly non-rigid in that the component can shrink in size, grow in size, or change shape. Nevertheless, the applicant has determined that, at least in many cases, the various components as comprise a particular view of a patient will vary sufficiently enough from one another to permit such components to be treated, for these present purposes, as rigid structures even when such a characterization constitutes a highly inaccurate characterization for most (or perhaps all) other purposes.

When the first information comprises, at least in part, the aforementioned segmentation information this step 103 can include, if desired, identifying one or more of the components in the second image by use of that segmentation information. This can facilitate, for example, identifying structures in the second image such as the patient's organs or treatment targets such as one or more tumors. When pursuing this approach, this correlation step can include, for example, identifying the components in the second image to thereby provide identified components while also determining relative positions amongst the identified components to perform a course registration with respect to the first image.

FIG. 4 provides a simple example to illustrate one corresponding approach in these regards. In this example, the patient's components 401 as captured in the first image 201 include a circle shape, a triangle shape, and a square shape. In addition, this first image 201 provides information regarding the relative position of these components, one to the other, as well as information regarding the relative orientation of these components to one another.

The second image 204 presents these same components 401. In the second image 204, however, each of the components 401 has moved somewhat relative to the positions shown in the first image 201. In addition, the component that is square shaped in the first image 201 has become an elongated-rectangle shape in the second image 204.

The image denoted by reference numeral 402 represents a straight-forward computational overlaying of one image on the other. In this example, the circle shape component for both images is relatively easy to correlate while the triangle shape component is more challenging due to very little overlap from one image to the other. The square shape component presents an even greater challenge as there not only is little overlap but the shape of the component has actually changed.

The image denoted by reference numeral 403 represents a course registration achieved by these teachings. By computationally treating these components as being rigid structures (even though, clearly, at least one of the components is not a rigid structure), a course but relatively computationally-easy registration step successfully correlates and registers the circle shape components in both images, the triangle shape components in both images, and the square/rectangle shape components in both images.

By one approach, if desired, the step 103 of correlating the various components of the first image with the second image can comprise, at least in part, correlating multiple components in parallel. This can comprise correlating only some of the multiple components in parallel or all of the components in parallel as desired. By separately registering, in parallel, different components in one image with their counterparts in another image, this process 100 can be concluded in a relatively short period of time. This, in turn, can help in reducing the delay between capturing the second image and beginning the updated/modified radiation-treatment plan.

In the simple illustrative examples provided above, this process 100 correlates discrete components in one image with the discrete components of another image. It may be noted, however, that in some application settings some or all of a plurality of such components may each comprise some corresponding part of a single organ. When the organ comprises a non-rigid structure, this process 100 will nevertheless treat various portions of such an organ as being rigid structures for the purpose of performing a course registration of those portions in a second image with counterparts in a first image.

This registration of components of the second image with components of the first image can then be utilized by the radiation-treatment planning apparatus to modify the pre-existing radiation-treatment plan accordingly. This can mean, for example, modifying the positions and times of the radiation-treatment machine to account for such things as internal movement of one or more of the components over time, shrinkage or enlargement of one or more of these components over time, and so forth. And this, in turn, can lead to a more assured delivery of the desired radiation dosage to the treatment volume while also tending to avoid delivering radiation to healthy body parts.

As already noted above, this correlation step 103 treats the patient's components as being rigid structures. A rigid structure, of course, will not tend to change its shape over time. If desired, this process 100 will accommodate an optional step 104 where the radiation-treatment planning apparatus performs finer-resolution registration of the contents of the two images by subsequently treating at least one of the components as a deformable component. This finer registration can address more complex deformation requirements as may be required by a particular radiation-treatment plan or methodology. Nevertheless, even in this case the preliminary use of a course-registration approach (that relies upon treating even non-rigid structures as rigid structures) can greatly simplify and shorten the finer-resolution calculations.

Figure 5:
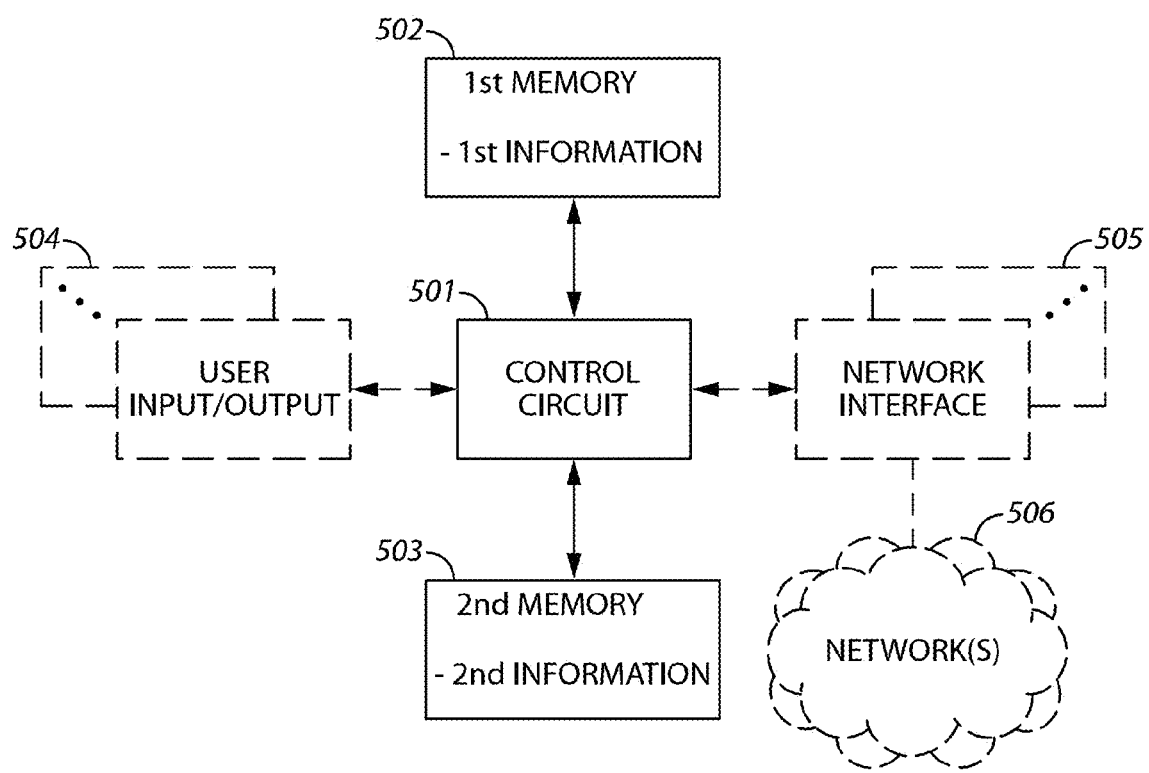
FIG. 5 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 5, an illustrative approach to such a platform 500 will now be provided.

In this illustrative example the platform 500 comprises a control circuit 501 that operably couples to a first memory 502 and to a second memory 503. This control circuit 501 can comprise a fixed-purpose hard-wired platform or can comprise a partially or wholly programmable platform. These architectural options are well known and understood in the art and require no further description here.

The first memory 502 stores the aforementioned first information regarding a first image as pertains to a patient's body at a first time. The second memory 503, in turn, stores the aforementioned second information regarding a second image as also pertains to the patient's body albeit at a second point in time that is later than the first time. (Those skilled in the art will recognize that these memories can comprise physically-discrete components as suggested by the illustration or can comprise parts of the same memory component (in which case the illustration can be taken as a logical rather than a physical depiction in these regards).) One or both of these memories can also store other programming or information of choice as desired. This can include, but is not limited to, executable computer code that, when executed by the control circuit 501, causes the control circuit 501 to carry out one or more of the steps, actions, or functions described herein.

The control circuit 501 can be configured (as suggested above by using, for example, corresponding programming when the control circuit 501 comprises a partially or wholly programmable platform) to carry out one or more of the steps, actions, or functions described herein as desired. This can include, by way of a non-limiting example, having the control circuit carry out the aforementioned correlation activity.

Depending upon the application setting this platform 500 can optionally include other components as desired. This can include, for example, any of a variety of user input and/or output mechanisms 504. Examples include keyboards, key pads, cursor-control mechanisms, touch-screen displays, and so forth. Examples also include active displays, printers, and so forth. This platform 500 can also optionally include one or more network interfaces 505 to permit, for example, the control circuit 501 to forward information, or to receive information from or via one or more networks 506 (including but not limited to the Internet and any of a variety of resources or servers as may be coupled thereto).

Such a platform 500 may be comprised of a plurality of physically distinct elements as is suggested by the illustration shown in FIG. 5. It is also possible, however, to view this illustration as comprising a logical view, in which case one or more of these elements can be enabled and realized via a shared platform.

Figure 6:
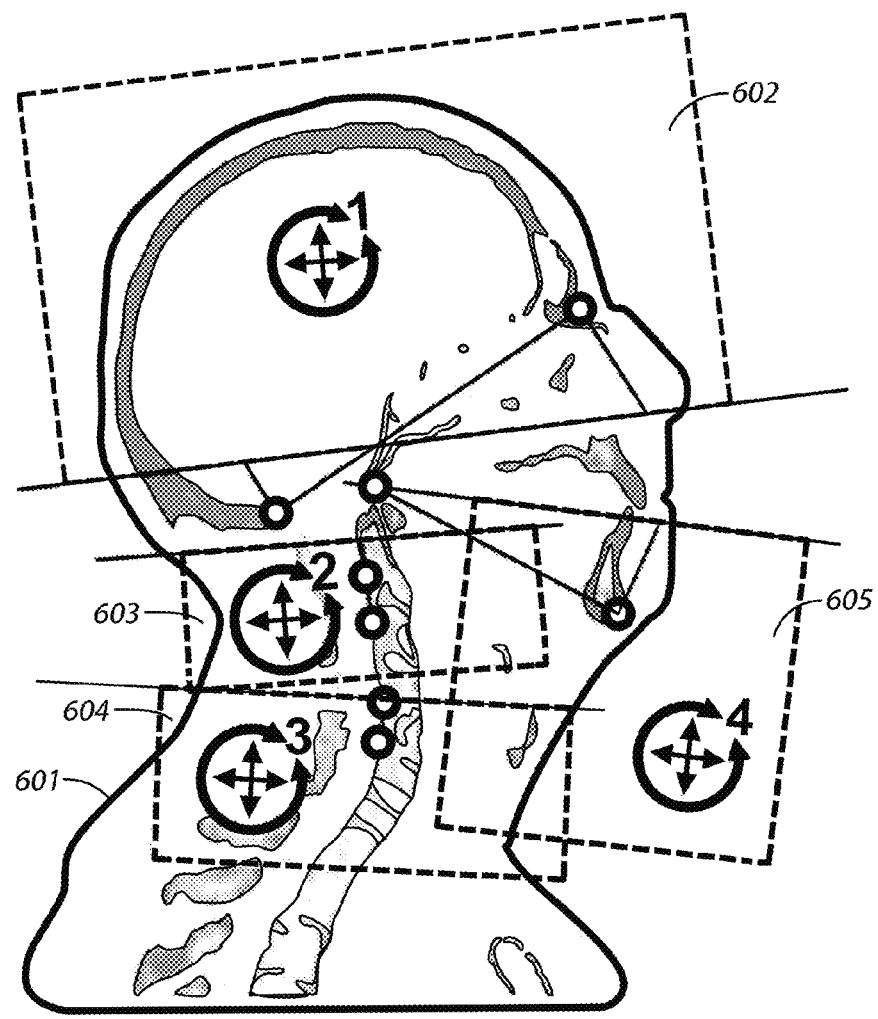
FIG. 6 comprises a side-elevational representation as configured in accordance with various embodiments of the invention.

These teachings are highly flexible and will accommodate considerable variations in practice without departing from the general precepts set forth above. FIG. 6 provides an illustrative example in these regards. (It will be understood that no specific limitations are intended by the specificity and particulars of this example.)

In this example, which works with an x-ray image of a patient's head and upper spine area 601, registration accuracy is improved by rigidly transforming multiple anatomical sub-volumes and interpolating between those sub-volumes. These sub-volumes are denoted as boxed areas in FIG. 6 with each being denoted generally by a sub-volume identifier 1 through 4. Sub-volume 1 602 includes the patient's upper skull, sub-volume 2 603 includes the patient's upper spine, sub-volume 3 604 includes the patient's lower spine, and sub-volume 4 605 includes the patient's chin. These teachings do not require that these sub-volumes be fully discrete from one another. For example, as illustrated, sub-volume 4 605 overlaps in part with both sub-volume 2 603 and sub-volume 3 604.

In this example, these sub-volumes are algorithmically represented as geometric primitives (in particular, planes and cylinders). These geometric primitives, in turn, are based on ten landmarks (with eight of these landmarks being shown in this illustration as small circles). These landmarks can be automatically detected (using known knowledge-based feature recognition methodologies) and correlate to the patient's mandible anterior, left, and right, the patient's eye centers, and the patient's foramen magnum posterior, C2, and C5 superior/interior bones.

To make the desired correlation these sub-volumes are transformed using a rigid mutual information matching algorithm that begins with an alignment of these landmarks. Mappings for points outside these sub-volumes (and within overlapping areas) are then calculated using interpolation.

Generally speaking, the foregoing permits elastic registration of volumetric images where the elastic registration denotes the determination of a point-to-point relationship (i.e., a so-called deformation field) between a source image of a given volume and a target volume image. This approach is sufficiently flexible to accommodate images of different subjects (or even of a subject and an artificial model of a subject) in addition to the previously-described images of a same subject. This approach is also sufficiently flexible to accommodate significantly different subject poses as well as rigid body rotations of parts of the patient.

This flexibility stems, at least in part, by the described initial alignment of multiple components that are treated as rigid bodies. This approach can provide, for example, better starting conditions for a subsequent standard elastic registration algorithm that yields the final result.

Figure 7:
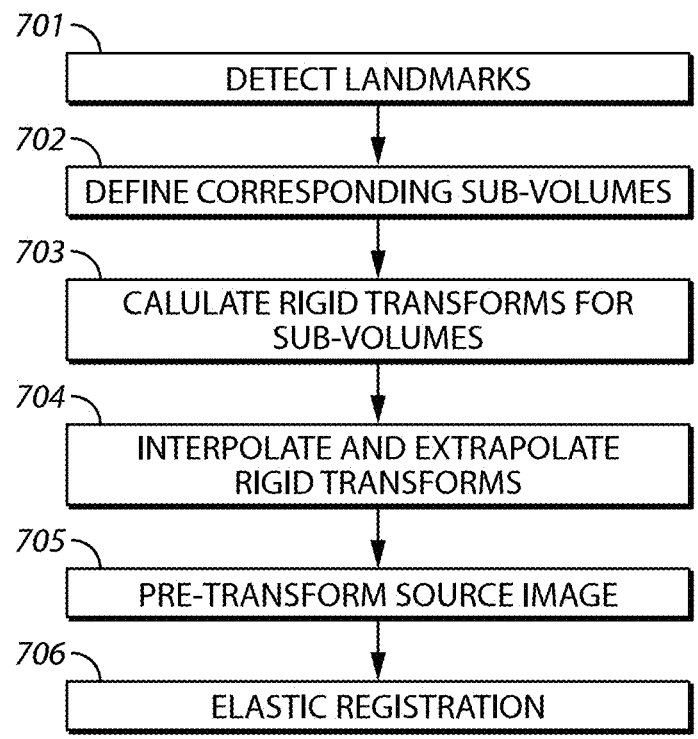
FIG. 7 comprises a flow diagram as configured in accordance with various embodiments of the invention.

FIG. 7 illustrates a process 700 that corresponds to such an approach. At step 701 this process 700 automatically (via, for example, an appropriate control circuit) detecting landmarks of interest in both a source image and a target image. (These teachings will accommodate non-automatic detection or specification of one or more of the landmarks if desired.)

At step 702 this process 700 then automatically defines pairs (i.e., corresponding) of sub-volumes as appear in both images based upon the detected landmarks. These sub-volumes serve to crop the source and target images prior to the rigid registration step 703 described below. These sub-volumes also define boundaries for the interpolation and extrapolation step 704 described below. In addition, these sub-volumes serve, at least in part, to permit describing articulation of displayed components in the source and target images. (Articulation refers to independent rotation and/or displacement.) Relevant components in these regards include, but are not limited to, parts of the body that surround a rigid bone and, in particular, areas where a joint exists between two neighboring sub-volumes.

Depending upon the application setting the selection of an adequate set of sub-volumes can influence the obtained results. This, in turn, can rely in some cases upon an adequate set of landmarks and choices regarding dividing surfaces or boundaries that can be described by use of these landmarks. To some extent, in many cases the number of landmarks needed to adequately define a sub-volume can depend on the dividing surfaces used to describe the sub-volume itself. Generally speaking, at least three landmarks are typically needed to define a plane in three-dimensional space whereas at least two landmarks are typically needed to define a cylinder (presuming that the cylinder's diameter can be a predefined constant or can be calculated from available information (such as distances pertaining to the two landmarks). Note, however, that the landmarks do not themselves need to lie on the dividing surfaces they define.

By way of illustration, in the case where the head and neck of the patient represents the volume of interest, a single plane can serve to divide the upper skull from the rest of the patient's body. In addition, two spinal cord sub-volumes can be defined using a cylinder and two planes each.

At step 703 this process 700 then determines a rigid transformation for each pair of defined sub-volumes. This can comprise, for example, using a standard 3D-3D rigid-image registration algorithm.

Step 704 then provides an elastic pre-alignment of the two images by using these rigid transformations to interpolate information in regions where sub-volumes overlap and to extrapolate information in regions that are external to any sub-volume. (Such transforms may not always be completely independent of one another as when, for example, two sub-volumes are connected by a joint. For the described registration purposes, however, that inherent dependency does not require detailed description or understanding.)

Figure 8:
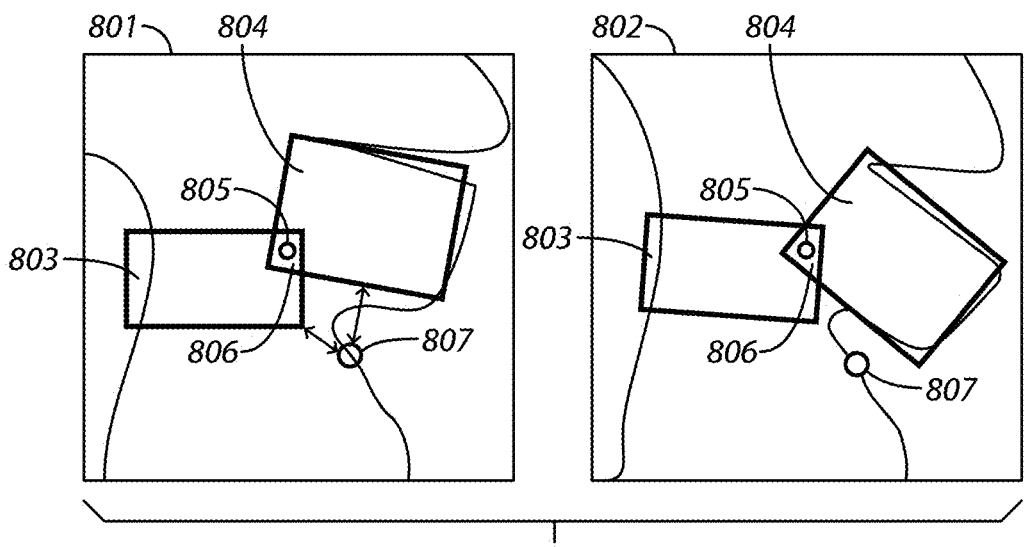
FIG. 8 depicts source and target images in accordance with various embodiments of the invention.

FIG. 8 provides a simple illustrative example in these regards. Here, for the sake of simplicity, the source/target images 801/802 have only two sub-volumes 803 and 804. In this example the patient's mouth opens further in the target image 802 than in the source image 801 and hence the second sub-volume 804 has pivoted about a first landmark 805 that lies in an overlapping region 806. An outlying landmark 807, in combination with the first landmark 806, can be used to calculate the transformation of the second sub-volume 804 as a result of the patient's different mouth position. This might comprise, for example, determining (for landmarks external to sub-volumes) a shortest distance to the sub-volume's boundary. (By one approach, the resultant transforms can be linearly combined albeit by also using the inverse square of the respective distance as a weight factor.)

At step 705 a standard 3D-3D elastic image registration algorithm can serve to register the pre-aligned source image with the target image. Step 706 then yields the elastic registration result (i.e., a final point relationship that comprises a composition of the pre-alignment results and the application of the foregoing elastic image registration algorithm.

Automatically-detected landmark positions (determined using such an approach) were compared with eight manually-set positions for each of 187 computed tomography scans from a number of different sources. The results were impressive. Automatic-landmark detection succeeded in 97% of these instances when differences were within a 6 mm radius.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. These approaches, for example, can be performed in real-time or near-real-time application settings. This can include real-time performance in an adaptive application setting (that relies, for example, upon Dynamic Adaptive RadioTherapy (DART) methodologies). As another example in these regards, these teachings can be employed well-prior to administering a radiation treatment (for example, during a treatment-planning phase), just prior to administering a radiation treatment (within, for example, thirty or sixty minutes of administering the treatment), or even during the administration of a radiation treatment.

I claim:

1. A method comprising:
by a radiation-treatment planning apparatus:
accessing first information regarding a first image pertaining to a patient's body at a first time;
accessing second information regarding a second image pertaining to the patient's body at a second time that is later than the first time;
correlating components of the patient's body as appear in the second image with components that appear in the first image while treating the components as comprising rigid structures regardless of whether the components are rigid structures or not by:
automatically detecting landmarks common to both the first and second image;
using the landmarks to automatically define corresponding pairs of sub-volumes that appear in both the first and second image;
determine a rigid transformation for each pair of the defined sub-volumes;
using the rigid transformations to interpolate information in regions where corresponding pairs of the sub-volumes overlap and to extrapolate information in regions that are external to any of the sub-volumes.

2. The method of claim 1 wherein the sub-volumes comprise geometric primitives that only roughly correspond to their respective components of the patient's body.

3. The method of claim 2 wherein the geometric primitives comprises primitives selected from the group comprising planes and cylinders.

4. The method of claim 3 wherein using the landmarks to automatically define corresponding pairs of sub-volumes that appear in both the first and second image comprises using at least two landmarks when defining a sub-volume as a cylinder and at least three landmarks when defining a sub-volume as a plane.

5. The method of claim 1 wherein automatically defining the corresponding pairs of sub-volumes comprises, at least in part, cropping the first and second images.

6. The method of claim 1 wherein using the rigid transformations to interpolate information in regions where corresponding pairs of the sub-volumes overlap and to extrapolate information in regions that are external to any of the sub-volumes comprises using elastic pre-alignment of the first and second images using the rigid transformations to interpolate information in regions where corresponding pairs of the sub-volumes overlap and to extrapolate information in regions that are external to any of the sub-volumes.

7. The method of claim 6 further comprising:
using elastic image registration to register a pre-aligned one of the first and second images with a remaining one of the first and second images to register the first image with the second image.

* * * * *